(12) United States Patent
Sherwood et al.

(10) Patent No.: US 8,988,859 B2
(45) Date of Patent: Mar. 24, 2015

(54) SINTERED CAPACITOR ELECTRODE INCLUDING A FOLDED CONNECTION

(71) Applicant: Cardiac Pacemakers, Inc., St. Paul, MN (US)

(72) Inventors: Gregory J. Sherwood, North Oaks, MN (US); Jay E. Daley, Coon Rapids, MN (US); Mary M. Byron, Roseville, MN (US); Eric Stemen, Roseville, MN (US); Peter Jay Kuhn, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 117 days.

(21) Appl. No.: 13/753,023

(22) Filed: Jan. 29, 2013

(65) Prior Publication Data

US 2013/0141842 A1    Jun. 6, 2013

Related U.S. Application Data

(62) Division of application No. 12/968,555, filed on Dec. 15, 2010, now Pat. No. 8,619,408.

(60) Provisional application No. 61/288,076, filed on Dec. 18, 2009.

(51) Int. Cl.
*H01G 9/10* (2006.01)
*H01G 9/045* (2006.01)
(Continued)

(52) U.S. Cl.
CPC .............. *H01G 9/045* (2013.01); *H01G 9/008* (2013.01); *H01G 9/048* (2013.01); *H01G 9/052* (2013.01);
(Continued)

(58) Field of Classification Search
CPC ......... H01G 9/008; H01G 9/10; H01G 9/052; H01G 9/042; H01G 9/045
USPC ......... 361/508, 509, 516, 517, 518, 519, 512, 361/523–525; 607/5, 7, 9
See application file for complete search history.

(56) References Cited

U.S. PATENT DOCUMENTS 3,025,441 A    3/1962    West
3,331,759 A    7/1967    Middelhoek et al.
(Continued)

FOREIGN PATENT DOCUMENTS

EP    0877400 A1    11/1998
EP    1470267 B1    4/2009
(Continued)

OTHER PUBLICATIONS

"U.S. Appl. No. 12/968,555, Notice of Allowance mailed Nov. 23, 2012", 9 pgs.
(Continued)

*Primary Examiner* — Nguyen T Ha
(74) *Attorney, Agent, or Firm* — Schwegman Lundberg & Woessner, P.A.

(57) ABSTRACT

This document discusses capacitive elements including a first, second and third electrode arranged in a stack. The third electrode is positioned between the first and second electrode. An interconnect includes a unitary substrate shared with the first and second electrodes. The interconnect is adapted to deform to accommodate the stacked nature of the first and second electrodes. The unitary substrate includes a sintered material disposed thereon.

20 Claims, 14 Drawing Sheets

(51) Int. Cl.
*H01G 9/008* (2006.01)
*H01G 9/048* (2006.01)
*H01G 9/052* (2006.01)
*H01G 9/06* (2006.01)
*H01G 9/08* (2006.01)
*H01G 9/14* (2006.01)
*H01G 9/00* (2006.01)
*H01G 9/15* (2006.01)
*A61N 1/375* (2006.01)
*A61N 1/378* (2006.01)

(52) U.S. Cl.
CPC . *H01G 9/06* (2013.01); *H01G 9/08* (2013.01); *H01G 9/14* (2013.01); *H01G 9/0029* (2013.01); *H01G 9/15* (2013.01); *A61N 1/375* (2013.01); *A61N 1/3782* (2013.01)
USPC ........... 361/518; 361/516; 361/517; 361/519; 361/508; 361/509

(56) References Cited

U.S. PATENT DOCUMENTS

| | | | |
|---|---|---|---|
| 3,445,731 A | 5/1969 | Saeki et al. |
| 3,627,520 A | 12/1971 | Rogers |
| 3,638,083 A | 1/1972 | Dornfeld et al. |
| 3,644,796 A | 2/1972 | Carino |
| 3,647,415 A | 3/1972 | Yano et al. |
| 3,789,502 A | 2/1974 | Callins et al. |
| 4,059,116 A | 11/1977 | Adams |
| 4,085,397 A | 4/1978 | Yagher, Jr. |
| 4,107,762 A | 8/1978 | Shirn et al. |
| 4,406,286 A | 9/1983 | Stein |
| 4,442,473 A | 4/1984 | Holtzman et al. |
| 4,687,951 A | 8/1987 | McElroy |
| 4,720,767 A | 1/1988 | Chan et al. |
| 4,840,122 A | 6/1989 | Nerheim |
| 4,882,115 A | 11/1989 | Schmickl |
| 4,894,746 A | 1/1990 | Mori et al. |
| 5,062,025 A | 10/1991 | Verhoeven et al. |
| 5,115,378 A | 5/1992 | Tsuchiya et al. |
| RE34,879 E | 3/1995 | Bocchi et al. |
| 5,468,254 A | 11/1995 | Hahn et al. |
| 5,591,211 A | 1/1997 | Meltzer |
| 5,591,217 A | 1/1997 | Barreras |
| 5,634,938 A | 6/1997 | Swanson et al. |
| 5,660,737 A | 8/1997 | Elias et al. |
| 5,763,911 A | 6/1998 | Matthews et al. |
| 5,807,397 A | 9/1998 | Barreras |
| 5,874,770 A | 2/1999 | Saia et al. |
| 5,930,109 A | 7/1999 | Fishler |
| 6,115,235 A | 9/2000 | Naito |
| 6,141,205 A | 10/2000 | Nutzman et al. |
| 6,161,040 A | 12/2000 | Blunsden |
| 6,193,779 B1 | 2/2001 | Reichert et al. |
| 6,241,751 B1 | 6/2001 | Morgan et al. |
| 6,310,757 B1 | 10/2001 | Tuzuki et al. |
| 6,347,032 B2 | 2/2002 | Naito |
| 6,350,406 B1 | 2/2002 | Satou et al. |
| 6,351,371 B1 | 2/2002 | Yoshida et al. |
| 6,385,031 B1 | 5/2002 | Lerche et al. |
| 6,456,877 B1 | 9/2002 | Fishler |
| 6,459,566 B1 | 10/2002 | Casby et al. |
| 6,493,212 B1 | 12/2002 | Clarke et al. |
| 6,509,588 B1 | 1/2003 | O'Phelan et al. |
| 6,560,089 B2 | 5/2003 | Miltich et al. |
| 6,678,559 B1 | 1/2004 | Breyen et al. |
| 6,687,118 B1 | 2/2004 | O'Phelan et al. |
| 6,699,265 B1 | 3/2004 | O'Phelan et al. |
| 6,775,127 B2 | 8/2004 | Yoshida |
| 6,778,860 B2 | 8/2004 | Ostroff et al. |
| 6,785,123 B2 | 8/2004 | Keser |
| 6,801,424 B1 | 10/2004 | Nielsen et al. |
| 6,807,048 B1 | 10/2004 | Nielsen et al. |
| 6,850,405 B1 * | 2/2005 | Mileham et al. ............ 361/302 |
| 6,855,234 B2 | 2/2005 | D'Astolfo, Jr. |
| 6,865,417 B2 | 3/2005 | Rissmann et al. |
| 6,914,769 B2 | 7/2005 | Welsch et al. |
| 6,952,608 B2 | 10/2005 | Ostroff |
| 6,954,670 B2 | 10/2005 | Ostroff |
| 7,024,246 B2 | 4/2006 | Acosta et al. |
| 7,327,557 B2 | 2/2008 | Poplett |
| 7,522,957 B2 | 4/2009 | Ostroff |
| 7,531,010 B1 | 5/2009 | Feger et al. |
| 7,564,677 B2 | 7/2009 | Poplett |
| 7,760,488 B2 | 7/2010 | Breznova et al. |
| 7,856,265 B2 | 12/2010 | Linder et al. |
| 8,179,663 B2 | 5/2012 | Brabeck et al. |
| 8,619,408 B2 | 12/2013 | Sherwood et al. |
| 8,725,252 B2 | 5/2014 | Sherwood |
| 8,873,220 B2 | 10/2014 | Sherwood et al. |
| 2003/0169560 A1 | 9/2003 | Welsch et al. |
| 2004/0147960 A1 | 7/2004 | O'Phelan et al. |
| 2004/0147961 A1 | 7/2004 | O'Phelan et al. |
| 2004/0240155 A1 | 12/2004 | Miltich et al. |
| 2005/0017888 A1 | 1/2005 | Sherwood et al. |
| 2006/0035152 A1 | 2/2006 | Nishimura et al. |
| 2006/0139580 A1 | 6/2006 | Conner et al. |
| 2006/0139850 A1 | 6/2006 | Rorvick et al. |
| 2006/0166088 A1 | 7/2006 | Hokanson et al. |
| 2006/0174463 A1 | 8/2006 | O'Phelan et al. |
| 2006/0249774 A1 | 11/2006 | Sherwood |
| 2007/0109723 A1 | 5/2007 | Kuriyama et al. |
| 2007/0109727 A1 | 5/2007 | Edson et al. |
| 2007/0188980 A1 | 8/2007 | Hossick-Schott |
| 2008/0030927 A1 | 2/2008 | Sherwood |
| 2008/0170354 A1 | 7/2008 | Dvorak et al. |
| 2008/0198534 A1 | 8/2008 | Lee et al. |
| 2008/0208270 A1 | 8/2008 | Linder et al. |
| 2009/0231782 A1 | 9/2009 | Fujita et al. |
| 2009/0237862 A1 | 9/2009 | Nielsen et al. |
| 2009/0242415 A1 | 10/2009 | Yoshimitsu |
| 2009/0273884 A1 | 11/2009 | Shimizu et al. |
| 2010/0010562 A1 | 1/2010 | Daley et al. |
| 2010/0110614 A1 | 5/2010 | Umemoto et al. |
| 2010/0110615 A1 | 5/2010 | Nishimura et al. |
| 2010/0157510 A1 | 6/2010 | Miyachi et al. |
| 2010/0193731 A1 | 8/2010 | Lee et al. |
| 2010/0195261 A1 | 8/2010 | Sweeney et al. |
| 2010/0226066 A1 | 9/2010 | Sweeney et al. |
| 2010/0226070 A1 | 9/2010 | Yang et al. |
| 2011/0038098 A1 | 2/2011 | Taira et al. |
| 2011/0149474 A1 | 6/2011 | Sherwood et al. |
| 2011/0149475 A1 | 6/2011 | Sherwood et al. |
| 2011/0152958 A1 | 6/2011 | Sherwood et al. |
| 2011/0152959 A1 | 6/2011 | Sherwood |
| 2011/0152960 A1 | 6/2011 | Daley et al. |
| 2011/0152961 A1 | 6/2011 | Sherwood |
| 2011/0317370 A1 | 12/2011 | Sherwood |

FOREIGN PATENT DOCUMENTS

| | | |
|---|---|---|
| JP | 2003522420 A | 7/2013 |
| WO | WO-2006139850 A1 | 6/2006 |
| WO | WO-2011075506 A2 | 6/2011 |
| WO | WO-2011075506 A3 | 6/2011 |
| WO | WO-2011075508 A2 | 6/2011 |
| WO | WO-2011075508 A3 | 6/2011 |
| WO | WO-2011075511 A2 | 6/2011 |
| WO | WO-2011075511 A3 | 6/2011 |

OTHER PUBLICATIONS

"U.S. Appl. No. 12/968,555, Response filed Oct. 29, 2012 to Restriction Requirement mailed Sep. 27, 2012", 7 pgs.

"U.S. Appl. No. 12/968,555, Restriction Requirement mailed Sep. 27, 2012", 7 pgs.

"U.S. Appl. No. 12/968,555, Supplemental Notice of Allowability mailed Dec. 26, 2012", 2 pgs.

"International Application Serial No. PCT/US2010/060432, Corrected International Preliminary Report on Patentability mailed May 11, 2012", 22 pgs.

"International Application Serial No. PCT/US2010/060432, International Preliminary Report on Patentability mailed Apr. 27, 2012", 16 pgs.

(56) References Cited

OTHER PUBLICATIONS

"International Application Serial No. PCT/US2010/060432, Invitation to Pay Additional Fees mailed Sep. 13, 2011", 9 pgs.
"International Application Serial No. PCT/US2010/060432, Search Report mailed Dec. 5, 2011", 6 pgs.
"International Application Serial No. PCT/US2010/060432, Written Opinion mailed Dec. 5, 2011", 14 pgs.
"International Application Serial No. PCT/US2010/060437, International Preliminary Report on Patentability", 7 pgs.
"International Application Serial No. PCT/US2010/060437, Search Report mailed Sep. 13, 2011", 4 pgs.
"International Application Serial No. PCT/US2010/060437, Written Opinion mailed Sep. 13, 2011", 6 pgs.
"International Application Serial No. PCT/US2010/060444, International Preliminary Report on Patentability mailed Jun. 28, 2012", 8 pgs.
"International Application Serial No. PCT/US2010/060444, International Search Report mailed Sep. 14, 2011", 4 pgs.
"International Application Serial No. PCT/US2011/060444, Written Opinion mailed Sep. 14, 2011", 7 pgs.
Bocek, Joseph M, et al., "Method and Apparatus for Charging Partitioned Capacitors", U.S. Appl. No. 11/462,301, filed Aug. 3, 2006, 53 pgs.
US 8,503,164, 8/2013, Sherwood et al. (withdrawn).
"U.S. Appl. No. 12/968,523, Response filed Sep. 23, 2013 to Non Final Office Action mailed Jun. 21, 2013", 8 pgs.
"U.S. Appl. No. 12/968,523, Advisory Action mailed Sep. 22, 2014", 3 pgs.
"U.S. Appl. No. 12/968,523, Final Office Action mailed Jun. 20, 2014", 7 pgs.
"U.S. Appl. No. 12/968,523, Non Final Office Action mailed Jun. 21, 2013", 12 pgs.
"U.S. Appl. No. 12/968,523, Non Final Office Action mailed Oct. 15, 2013", 9 pgs.
"U.S. Appl. No. 12/968,523, Response filed Jan. 8, 2014 to Non-Final Office Action mailed Oct. 15, 2013", 11 pgs.
"U.S. Appl. No. 12/968,523, Response filed Aug. 18, 2014 to Final Office Action mailed Jun. 20, 2014", 7 pgs.
"U.S. Appl. No. 12/968,536, Response filed Sep. 23, 2013 to Non Final Office Action mailed Jun. 21, 2013", 7 pgs.
"U.S. Appl. No. 12/968,536, Advisory Action mailed Sep. 19, 2014", 3 pgs.
"U.S. Appl. No. 12/968,536, Final Office Action mailed Jun. 19, 2014", 9 pgs.
"U.S. Appl. No. 12/968,536, Non Final Office Action mailed Jun. 21, 2013", 7 pgs.
"U.S. Appl. No. 12/968,536, Non Final Office Action mailed Oct. 2, 2013", 17 pgs.
"U.S. Appl. No. 12/968,536, Response filed Jan. 2, 2014 to Non-Final Office Action mailed Oct. 2, 2013", 10 pgs.
"U.S. Appl. No. 12/968,536, Response filed Aug. 18, 2014 to Final Office Action mailed Jun. 19, 2014", 8 pgs.
"U.S. Appl. No. 12/968,555, Notice of Allowance mailed Apr. 2, 2013", 9 pgs.
"U.S. Appl. No. 12/968,555, Notice of Allowance mailed Aug. 28, 2013", 8 pgs.
"U.S. Appl. No. 12/968,561, Notice of Allowance mailed Nov. 13, 2013", 11 pgs.
"U.S. Appl. No. 12/968,561, Response filed Jul. 31, 2013 to Restriction Requirement mailed Jun. 21, 2013", 7 pgs.
"U.S. Appl. No. 12/968,561, Response filed Sep. 30, 2013 to Restriction Requirement mailed Aug. 29, 2013", 7 pgs.
"U.S. Appl. No. 12/968,561, Restriction Requirement mailed Jun. 21, 2013", 6 pgs.
"U.S. Appl. No. 12/968,561, Restriction Requirement mailed Aug. 29, 2013", 7 pgs.
"U.S. Appl. No. 12/968,571, Response filed Apr. 3, 2013 to Non Final Office Action mailed Nov. 9, 2012", 13 pgs.
"U.S. Appl. No. 12/968,571, Advisory Action mailed Jun. 3, 2014", 3 pgs.
"U.S. Appl. No. 12/968,571, Advisory Action mailed Aug. 22, 2013", 3 pgs.
"U.S. Appl. No. 12/968,571, Final Office Action mailed Mar. 11, 2014", 15 pgs.
"U.S. Appl. No. 12/968,571, Final Office Action mailed Jun. 3, 2013", 14 pgs.
"U.S. Appl. No. 12/968,571, Non Final Office Action mailed Sep. 13, 2013", 15 pgs.
"U.S. Appl. No. 12/968,571, Non Final Office Action mailed Nov. 9, 2012", 15 pgs.
"U.S. Appl. No. 12/968,571, Notice of Allowance mailed Jun. 26, 2014", 7 pgs.
"U.S. Appl. No. 12/968,571, Response filed May 12, 2014 to Final Office Action mailed Mar. 11, 2014", 9 pgs.
"U.S. Appl. No. 12/968,571, Response filed Jun. 10, 2014 to Final Office Action mailed Mar. 11, 2014", 6 pgs.
"U.S. Appl. No. 12/968,571, Response filed Jul. 31, 2013 to Final Office Action mailed Jun. 3, 2013", 11 pgs.
"U.S. Appl. No. 12/968,584, Response filed Oct. 29, 2013 to Non Final Office Action malled Jul. 31, 2013", 10 pgs.
"U.S. Appl. No. 12/968,584, Non Final Office Action mailed Jan. 30, 2013", 11 pgs.
"U.S. Appl. No. 12/968,584, Non Final Office Action mailed Jul. 31, 2013", 12 pgs.
"U.S. Appl. No. 12/968,584, Notice of Allowance mailed Dec. 27, 2013", 7 pgs.
"U.S. Appl. No. 12/968,584, Response filed Apr. 26, 2013 to Non Final Office Action mailed Jan. 30, 2013", 10 pgs.
"Japanese Application Serial No. 2012-544737, Office Action mailed Nov. 5, 2013", With English Translation, 6 pgs.

* cited by examiner

SINTERED CAPACITOR ELECTRODE INCLUDING A FOLDED CONNECTION

CROSS-REFERENCE TO RELATED APPLICATIONS

This application is a divisional of U.S. patent application Ser. No. 12/968,555, issued as U.S. Pat. No. 8,619,408, entitled "Sintered Capacitor Electrode Including a Folded Connection," filed Dec. 15, 2010, which claims the benefit of U.S. Provisional Application No. 61/288,076, filed on Dec. 18, 2009, under 35 U.S.C. §119(e), each of which is incorporated herein by reference in their entirety.

TECHNICAL FIELD

This document relates generally to energy storage and particularly to sintered electrodes to store energy in an implantable medical device.

BACKGROUND

Electrical stimulation therapy has been found to benefit some patients. For example, some patients suffer from an irregular heartbeat or arrhythmia and may benefit from application of electrical stimulation to the heart. Some patients suffer from a particular type of arrhythmia called a fibrillation. Fibrillations may affect different regions of the heart, such as the atria or the ventricles. When a fibrillation occurs in the ventricles, the heart's ability to pump blood is dramatically reduced, putting the patient at risk of harm. It has been found that applying an electrical stimulation to the patient can effectively treat patients suffering from disorders such as from fibrillation by restoring a regular heartbeat.

Because disorders such as fibrillations can happen at any time, it is helpful to have a device that is easily accessible to treat them. In some cases, it is helpful if that device is portable or implantable. In developing a device that is portable or implantable, it is helpful to have access to subcomponents that are compact and lightweight and that can perform to desired specifications.

SUMMARY

This document provides apparatus related to energy storage devices having folded portions to couple electrodes of the devices. One apparatus embodiment includes a hermetically sealed capacitor case sealed to retain electrolyte, a first electrode disposed in the capacitor case, a second electrode disposed in the capacitor case in a stack with the first electrode, the second electrode including sintered material disposed on a flexible unitary substrate, with the flexible unitary substrate included a connection portion that is flexed and coupled to the first electrode. The apparatus includes, a third electrode disposed in the capacitor case in the stack, a first terminal coupled to the first electrode, and a second terminal coupled to the third electrode, the second terminal electrically isolated from the first terminal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
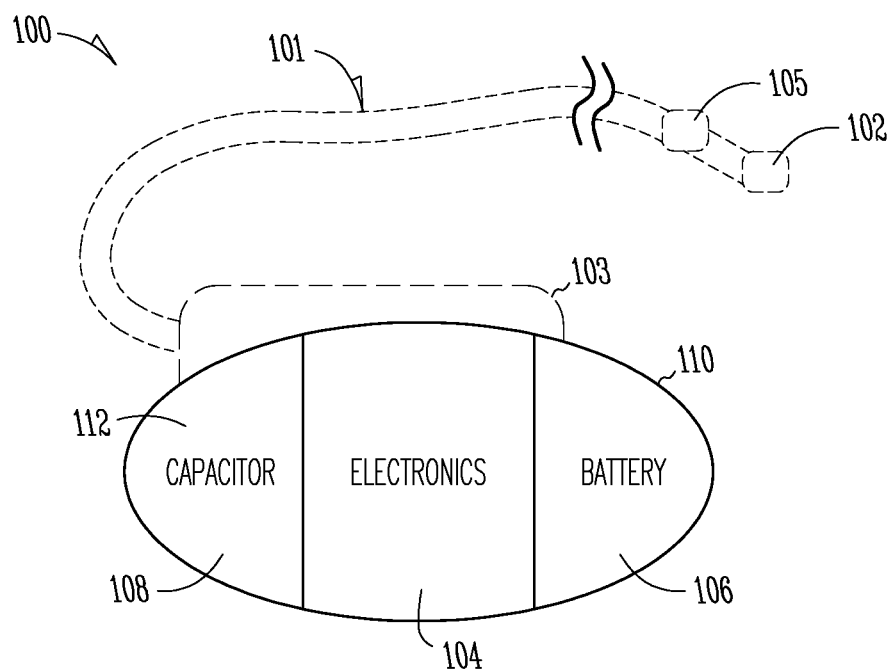
FIG. 1 is a schematic of a medical system including a sintered capacitor, according to some embodiments.

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This document concerns sintered electrodes for use in an electrical energy storage device. Specific examples include sintered anodes formed of aluminum or its alloys. Certain examples are for use in aluminum electrolytic capacitors. Examples include electrodes with a sintered portion disposed onto at least one side of a substrate. Some examples include a stack of electrodes in which the substrates of multiple electrodes are interconnected. This interconnection method improves upon energy storage devices using etched electrodes because the foils may be bent together for interconnection with a low risk of breakage, whereas etched materials often break. Additional benefits stem from an increased surface area that is a product of sintering.

Sintering results in many interstices (i.e., spaces) between grains of the electrode. Sintered electrodes resemble crushed grains with interstices between the grains. The interstices are filled with electrolyte, thereby increasing capacitance per unit of volume, as capacitance is proportional to a surface area exposed to electrolyte. An electrode with such interstices offers improved lateral or parallel movement of electrons in relation to a major surface of a flat electrode layer, as etched electrodes restrict lateral movement because the etchings result in voids that are typically perpendicular to the major surface of the flat layer. Accordingly, some examples have a lower ESR (equivalent series resistance) compared to etched foils due to this enhance ionic flow.

Overall, an energy storage device using the sintered electrodes described here is well suited for use in an implantable medical device such as a defibrillator. Because sintering can produce a variety of shapes, sintered electrodes can be used to create energy storage devices such as capacitors that have custom shapes versus simple cylinders or a prism having a parallelogram as its base. In some examples, manufacturing efficiency is improved, such as by allowing electrodes to be nested on a web before they are excised from the web and stacked into a capacitor. In other words, nesting reduces waste by allowing more of the web to be converted into electrodes. The interstices are very small, making the electrodes rigid and able to withstand handling by a machine or assembly personnel. These electrodes demonstrate an improved energy density over etched electrodes and are therefore useful to make smaller implantable devices that are able to deliver an amount of energy for a particular therapy.

FIG. 1 is a schematic of a medical system 100 including a sintered capacitor, according to some embodiments. The medical system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

Electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. The electronics 104 can be powered wirelessly using an inductor. Alternatively, the electronics 104 can be powered by a battery 106. In some examples, electronics 104 are to direct small therapeutic bursts of energy to a patient from the battery 106.

For therapies, such as defibrillation, that use energy discharge rates exceeding what battery 106 is able to provide, a capacitor 108 is used. Energy from the battery 106 is controlled by the electronics 104 to charge the capacitor 108. The capacitor 108 is controlled by the electronics 104 to discharge to a patient to treat the patient. In some examples, the capacitor 108 completely discharges to a patient, and in additional examples, the capacitor is switched on to provide therapeutic energy and switched off to truncate therapy delivery.

Some examples of a medical system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the lead system 101 use different numbers of stimulation electrodes and/or sensors in accordance with the needs of the therapy to be performed.

Additional examples function without a lead 101. Leadless examples can be positioned in contact with the tissue to be stimulated, or can be positioned proximal to tissue to shock the tissue to be stimulated through intermediary tissue. Leadless examples can be easier to implant and can be less expensive as they do not require the additional lead components. The housing 110 can be used as an electrode in leadless configurations.

In certain embodiments, the electronics 104 include an electronic cardiac rhythm management circuit coupled to the battery 106 and the capacitor 108 to discharge the capacitor 108 to provide a therapeutic defibrillation pulse. In some examples, the system 100 includes an anode and a cathode sized to deliver a defibrillation pulse of at least approximately 50 joules. Other configurations can deliver larger amounts of energy. Some configurations deliver less energy. In some examples, the energy level is predetermined to achieve a delivered energy level mandated by a governing body or standard associated with a geographic region, such as a European country. In an additional embodiment, the anode and cathode are sized to deliver a defibrillation pulse of at least approximately 60 joules. In some examples, this is the energy level is predetermined to achieve an energy level mandated by a governing body of another region, such as the United States. In some examples, electronics 104 are to control discharge of a defibrillation pulse so that the medical system 100 delivers only the energy mandated by the region in which the system 100 is used. In some examples, a pulse of 36 joules is delivered.

Packaging anodes and cathodes can reduce their efficiency. Interconnections between conductors coupled to electronics and to the electrodes of the capacitor 108 decrease efficiency, for example. Accordingly, anodes and cathodes are sized to compensate for decreases in efficiency. As such, in some embodiments, the capacitor 108 includes anodes and cathodes sized and packaged to deliver a defibrillation pulse of at least approximately 50 joules. Some are sized and packaged to deliver a defibrillation pulse of at least approximately 60 joules.

One characteristic of some sintered electrode examples is that at least one anode and a cathode have a DC capacitance that is approximately 23% greater than a AC capacitance for the at least one anode and the cathode of an etched capacitor that has 74.5 microfarads per cubic centimeter. In some examples, the at least one anode and the cathode have an AC capacitance of at least 96.7 microfarads per cubic centimeter at 445 total voltage. In some examples, this is comparable to an operating voltage of about 415 volts. This is a 30% improvement over an etched capacitor that has 74.5 microfarads per cubic centimeter. Total voltage is the voltage that allows 1 milliamp of leakage per square centimeter. Some examples are aged to 415 volts.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal. Several materials can be used to form case 112, including, but not limited to, aluminum, titanium, stainless steel, nickel, a polymeric material, or combinations of these materials. The case 112 is sealed to retain electrolyte. Various electrolytes can be used including, but not limited to, Suzuki-Techno Corporation electrolyte model 1184. The case 112 includes a seal, such as a resin based seal including but not limited to epoxy, in some examples. Some examples include a rubber seal to seal case portions to one another, or to seal subcomponents such as a feedthrough to one or more case portion. In some examples, case 112 is welded together from subcomponents. Some examples include a case that includes one or more backfill ports, but the present subject matter is not so limited.

A hermetically sealed device housing 110 is used to house components, such as the battery 106, the electronics 104, and the capacitor 108. Hermeticity is provided by welding components into the hermetically sealed device housing 110, in some examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The capacitor 108 is improved by the present electrode technology in part because it can be made smaller and with less expense. The improvement provided by these electrodes is pertinent to any application where high-energy, high-voltage, or space-efficient capacitors are desirable, including, but not limited to, capacitors used for photographic flash equipment. The present subject matter extends to energy storage devices that benefit from high surface area sintered electrodes including, but not limited to, aluminum. The electrodes described here can be incorporated into cylindrical capacitors that are wound, in addition to stacked capacitors.

Figure 2:
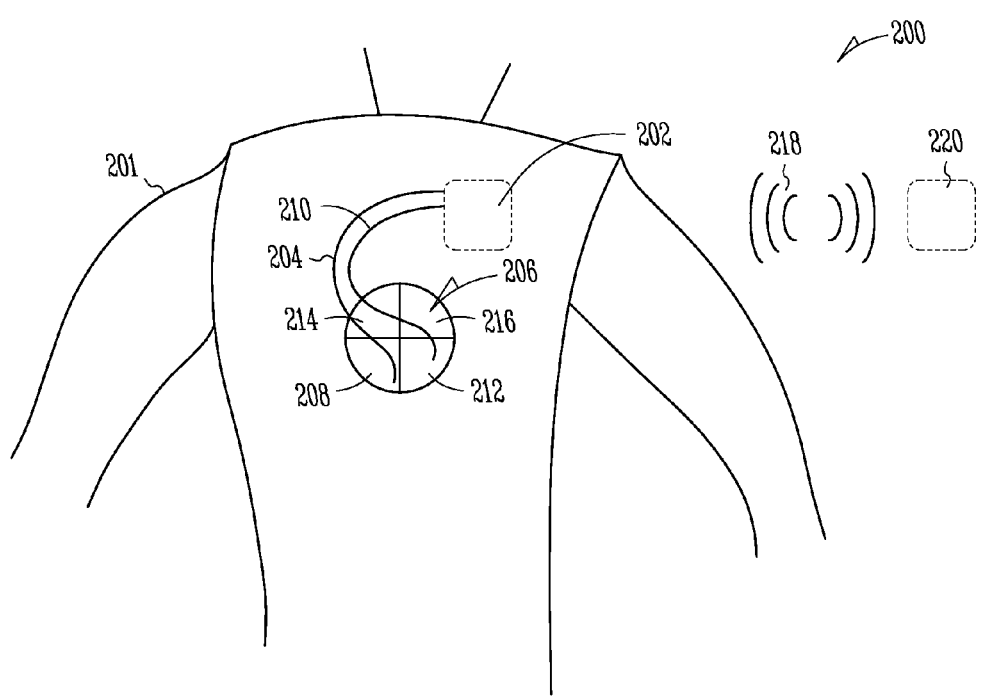
FIG. 2 is an implanted medical system including a sintered capacitor, according to some embodiments.

FIG. 2 is an implanted medical system 200, implanted in a patient 201, and including a sintered capacitor, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both those tissue regions. The second lead 210 is in direct contact with the left atrium 216 and the left ventricle 212 to sense and/or stimulate both those tissue regions. The cardiac rhythm management device 202 uses the lead electrodes to deliver energy to the heart, either between electrodes on the leads or between one or more lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202.

Figure 3:
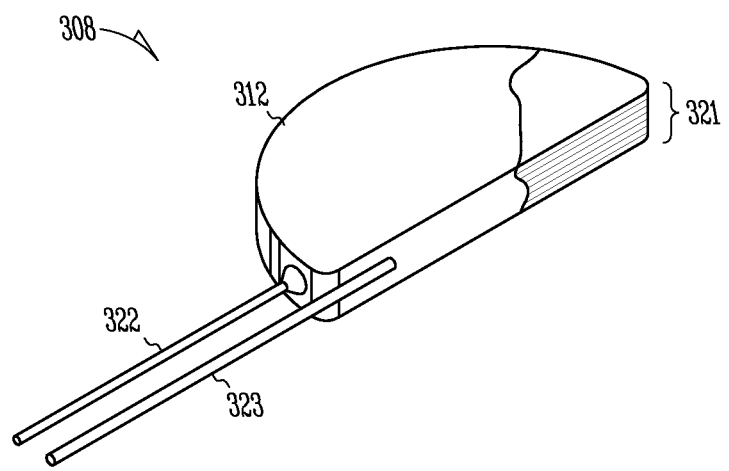
FIG. 3 shows a capacitor according to some embodiments of the present subject matter.

FIG. 3 shows a capacitor 308 according to some embodiments of the present subject matter. In some examples, the capacitor 308 is flat. Various embodiments include a plurality of electrode layers. Some examples include a plurality of electrodes aligned in a stack. Although the illustrated capacitor is "D" shaped, in other embodiments, the capacitor is shaped differently, including but not limited to, rectangular, circular, oval, square or other symmetrical or asymmetrical shapes. In various embodiments, a stack defines a custom three-dimensional form factor shaped to conform to an interior volume of a case such as a capacitor case. In some embodiments, the capacitor case 312 is made from conductive material such as aluminum. In other embodiments, the case 312 is made from non-conductive material such as ceramic or plastic.

In some examples, the capacitor 308 includes a first terminal 322 and a second terminal 323 to connect the capacitor stack 321 to an electrical component, such as an electrical component included in an implantable medical device. In some embodiments, a first terminal 322 is a feedthrough terminal insulated from the case, while the second terminal 323 is directly connected to the case. Other embodiments may incorporate other connection methods including, but not limited to, a different number of terminations and a different number of feedthroughs. In certain examples, the capacitor stack 321 includes one or more capacitor elements such as elements discussed here.

Figure 4A:
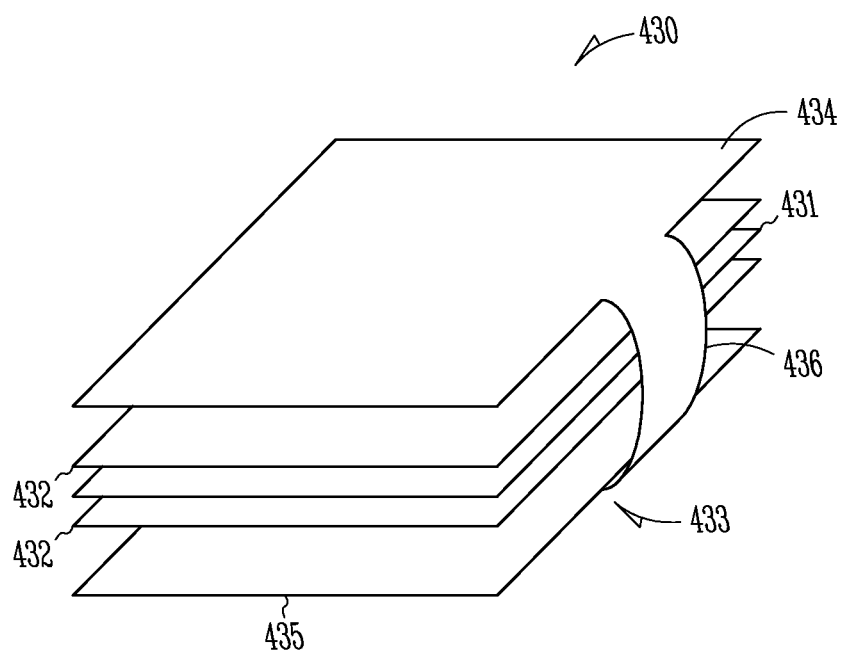
FIG. 4A shows an isometric view of a capacitor element according to some embodiments of the present subject matter.
Figure 4B:
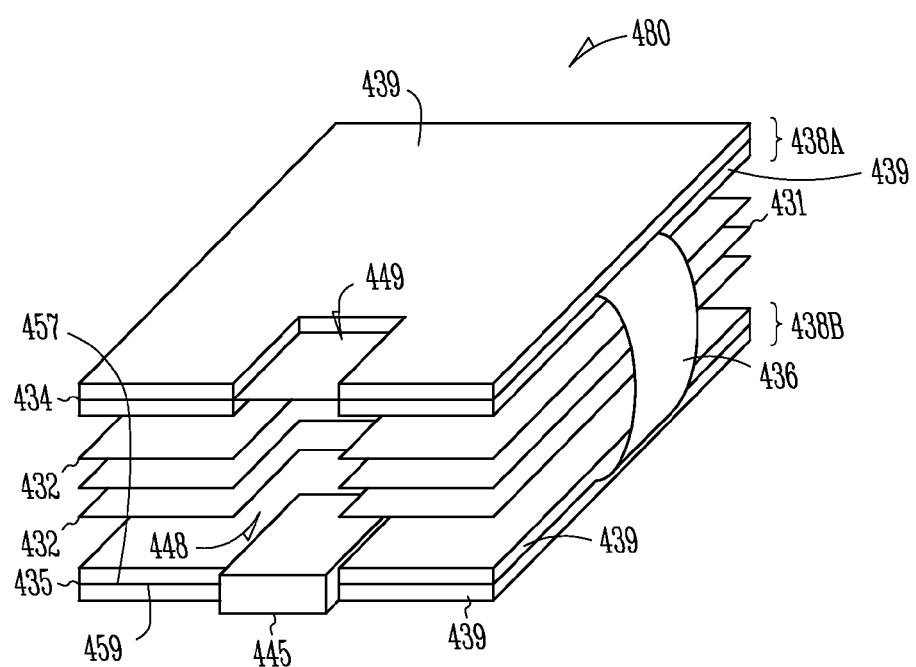
FIG. 4B shows an isometric view of a capacitor element according to some embodiments of the present subject matter.

FIG. 4A and 4B show an isometric view of a capacitor element 430 according to some embodiments of the present subject matter. One or more capacitor elements may be used in forming a capacitor stack. A capacitor element 430 includes a first electrode layer 431, separator material 432 proximate the first electrode layer, and a second electrode 433. The second electrode includes a second electrode layer substrate 434, a third electrode layer substrate 435 and a folded portion 436 coupling the second electrode layer substrate 434 and the third electrode layer substrate 435. The folded portion 436 folded upon itself to couple the substrates 434, 435 in the stacked configuration. In some examples, the second and third electrode layers 438a, 438b include sintered material 439 disposed on a substrate that is unsintered. In various embodiments, the substrate includes aluminum. In various embodiments, the sintered portion includes aluminum. The folded portion 436, in some embodiments, includes sintered material. In other embodiments, the folded portion includes one or more areas that are substantially free of sintering.

In some embodiments, the second electrode includes sintered material on one major surface 457 of the substrate. In various embodiments, the second electrode includes sintered material on both major surfaces 457, 459 of the substrate (see FIG. 4B). In various embodiments, the layers of the second electrode of a capacitor element are stacked such that perimeters of the substrate of each layer are substantially coextensive. In capacitors that may be made to fit a custom volume, the stacked electrodes may be offset to provide the desired shape. Some examples include a substantial overlap between adjacent electrodes.

In various embodiments, a layer may include a substantially sinter-free portion for connecting to other electrical components including other capacitor elements or other electrodes or electrode layers within the same capacitor element.

FIG. 4B shows a capacitor element 480 with a sintered electrode substrate and an interconnect according to some embodiments of the present subject matter. In some embodiments, components of the capacitor element, such as the first electrode layer 431 and the separator material 432, may be notched 448 to allow for connection to an adjacent element, other electronics or other capacitor elements. Such a notch 448 allows a connecting member 445 to be coupled to a target component without creating a bulge in components stacked onto the target component.

The illustrated embodiment of FIG. 4B shows a first electrode layer 431 and separator material 432 between a second electrode layer 438a and a third electrode layer 438b. The first electrode layer 431 and separator materials 432 include a notch 448 to accommodate connecting members coupled to the second 438a and third 438b electrode layers without creating a bulge in the stacked capacitor element 480. The second electrode layer illustrates a sinter-free area 449 for accommodating a connecting member to couple to the substrate of the second electrode layer 438a. The third electrode layer 438b shows a connecting member 445, such as a first clip, coupled to a sinter-free area of the third electrode layer 438b. Various embodiments include a second clip coupled to the first electrode layer. In such embodiments the first and second clips may be coupled together to interconnect the electrode layers. The clips may be coupled together, for example, using a weld. Other forms of coupling connecting members together are possible without departing from the scope of the present subject matter including, but not limited to, laser welding, ultrasonic welding, using conductive adhesive or combinations thereof. In various embodiments, the first electrode layer is a cathode and the second and third electrode layers include a first and second anode plate. In some embodiments, a slotted interconnect may be used to couple sinter-free portions of two or more electrode layers together. In various embodiments, an electrode includes a tab extending from the perimeter of the substrate of the electrode. In some embodiments, more than one tab may extend from the perimeter of the substrate of an electrode.

In various embodiments, a capacitor stack may include many tabs. The tabs may include various alignment arrangements to provide for various connections to capacitor terminations. In some embodiments, the tabs may be aligned vertically to allow for efficient interconnection of the corresponding capacitor electrodes. In some embodiments, some tabs may be aligned but offset from other aligned tabs to allow for separate interconnection such as for a partitioned capacitor. In various embodiments, tabs of varying width may be used. Tabs of varying width may be stacked such that a first tab fully overlaps a wider adjacent tab. Such an arrangement allows for efficient connection of adjacent tabs such as by using a cold weld. Additionally, such an arrangement forms a more rigid composite connection tab as additional wider tabs are stacked together.

Figure 5:
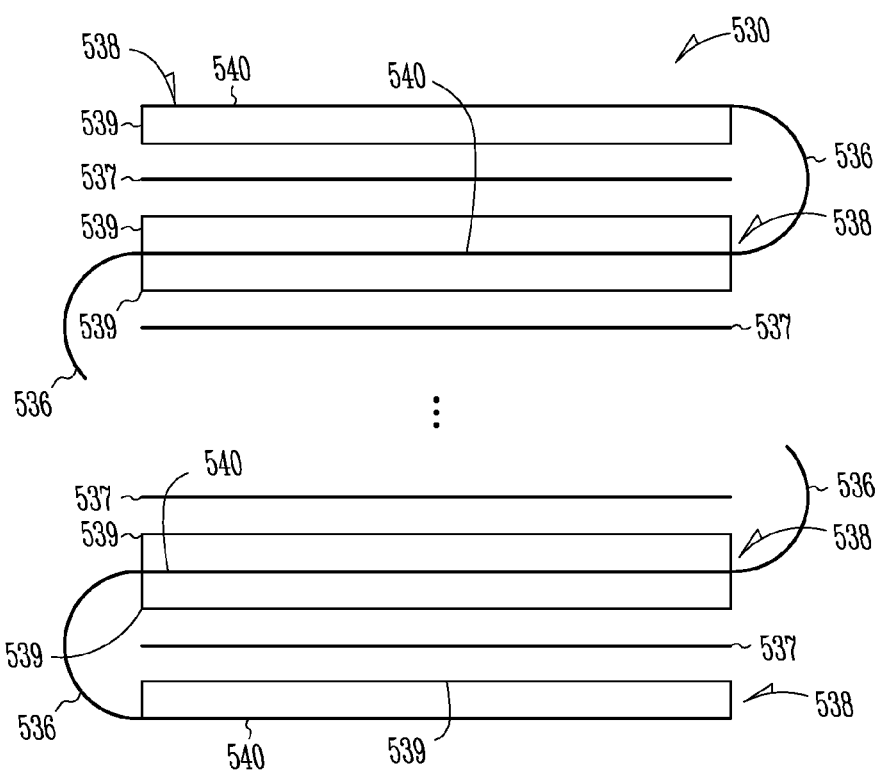
FIG. 5 shows a side view of a capacitor element according to some embodiments of the present subject matter.

FIG. 5 shows a side view of a capacitor element according to some embodiments of the present subject matter. The capacitor element 530 includes a number of cathode stacks 537 and a number of anode plates 538. Adjacent anode plates 538 are connected by a folding portion 536, according to some examples. Each anode plate includes a sintered portion 539 disposed on a substrate 540. In various embodiments, the substrate is a continuous, monolithic, solid, unitary piece of substrate material that forms a number of anode plates and folding portions of the capacitor element. In some embodiments, the substrate is a foil. In some examples, the substrate is an aluminum foil. Aluminum foil has a thickness of less than 0.008 inches/0.2 mm in various examples. Some aluminum foils are less than or equal to 0.005 inches thick. These foils are easily bent by hand and are easily torn by hand. Substrates that are thicker are additionally possible.

In some embodiments, the folding portion 536 connecting the anode plates 538 is separate from one or both of the anode plates it couples. In such embodiments, the folding portion 536 is coupled to an anode plate, for example using a weld, such as a cold weld, a laser weld or an ultrasonic weld or other coupling method. In some embodiments, the folding portion is coupled to a sinter free portion of the anode plate substrate. In various embodiments, one or more anode plates include sintered material disposed on both sides of the substrate. The cathode stack 537 includes a cathode. In various embodiments, the cathode stack 537 also includes separator material, such as separator material with absorbed or embedded electrolyte material.

Figure 6:
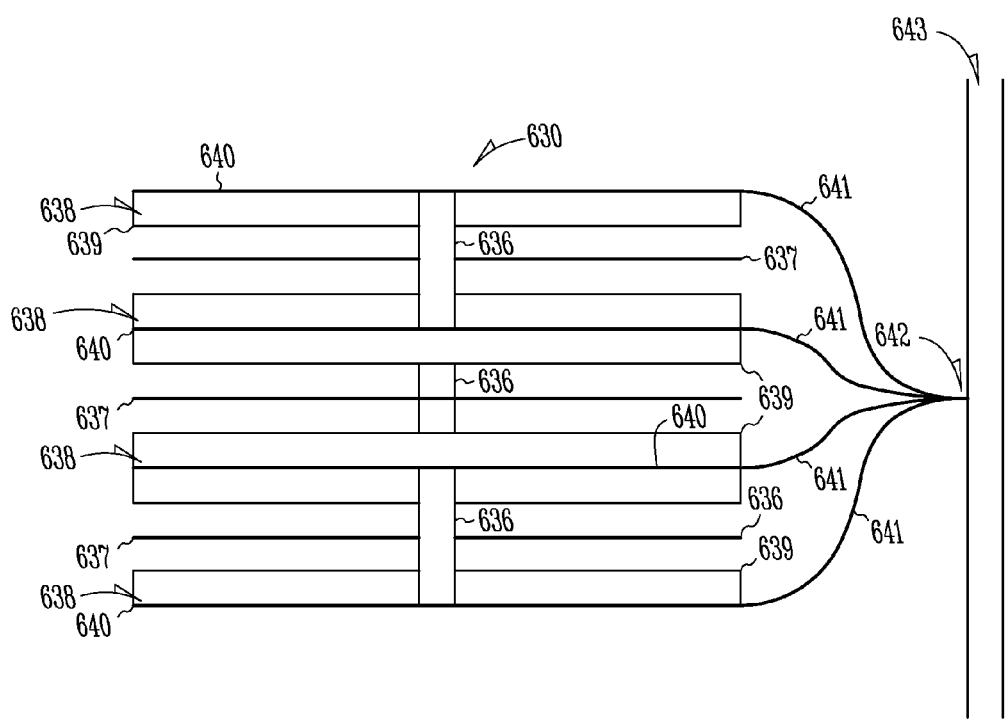
FIG. 6 shows a side view of a capacitor element according to some embodiments of the present subject matter.

FIG. 6 shows a side view of a capacitor element according to some embodiments of the present subject matter. The capacitor element 630 includes a number of cathode stacks 637, anode plates 638, folded portions 636 coupling anode plates, and anode tabs 641 coupled to the anode plates 638. In the illustrated embodiment, a number of anode tabs 641 are gathered and welded 642 for connection to electronics, such as electronics related to an implantable medical device. In some embodiments, one or more tabs are coupled to a case of capacitor 643.

The anode plates 638 include a sintered portion 639 disposed on a substrate 640, such as an aluminum substrate in some examples. In various embodiments, the anode tabs 641 are extensions of the substrate 640. In some embodiments, the anode tabs 641 are couple to the substrate, for example, the anode tabs may be coupled to the substrate of the anode plates at substantially sintering free portions of the substrate. In some embodiments, the tabs include sintered material disposed on a substrate.

Figure 7:
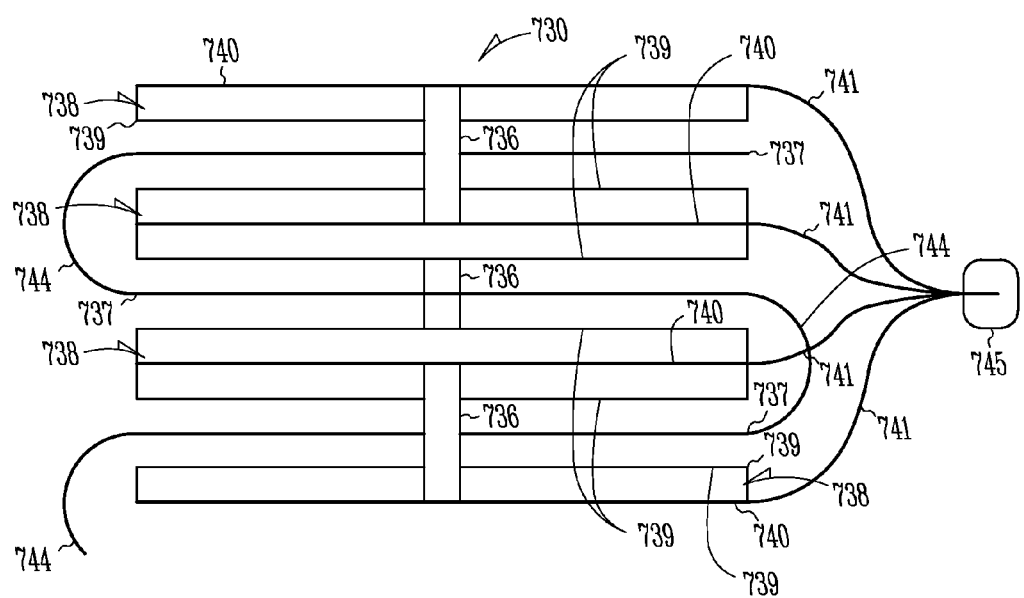
FIG. 7 shows a side view of a capacitor element according to some embodiments of the present subject matter.

FIG. 7 shows a side view of a capacitor element according to some embodiments of the present subject matter. The capacitor element 730 includes a number of cathode stacks 737, a number of anode plates 738, a number of folded portions 736 coupling anode plates, a number of folding portions 744 coupling cathode stacks and a number of tabs 741 for electrically coupling the anode plates 738 to each other using a clip 745. The clip 745 may be used to couple to other electronics, such as electronics related to an implantable medical device. In some embodiments, the clip 745 is coupled to a conductive case. In some embodiments, the clip 745 is coupled to a feedthrough of a case, where the feedthrough insulates the clip from the case. The cathode stack includes a cathode electrode, and may include separator material, such as separator material with absorbed or imbedded electrolyte material. The anode plates include sintered material 739 disposed on at least one major surface of an anode plate substrate 740. In various embodiments, sintered material is disposed on both major surfaces of an anode plate substrate. In various embodiments, the folded portions connecting the anode plates and the folded portions connecting the cathode stacks are continuous portions of the respective substrates of the anode plates and cathode stacks. Such an arrangement may provide efficiencies related to material and/or processing as each substrate can be excised from a continuous web of substrate material. It is understood that although the illustrated embodiment shows subsequent folding portions extending from opposite sides of the corresponding anode or cathode structure, other orientation arrangements are possible, as are other anode and cathode substrate shapes, without departing from the scope of the present subject matter.

Figure 8A:
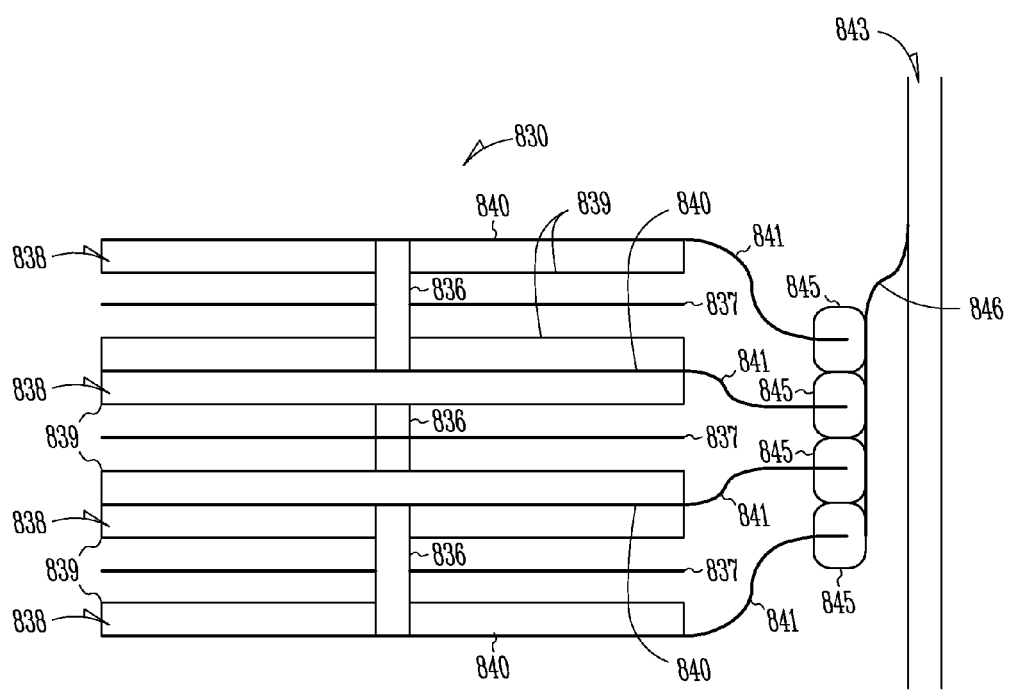
FIGS. 8A and 8B show side views of a capacitor element according to some embodiments of the present subject matter.
Figure 8B:
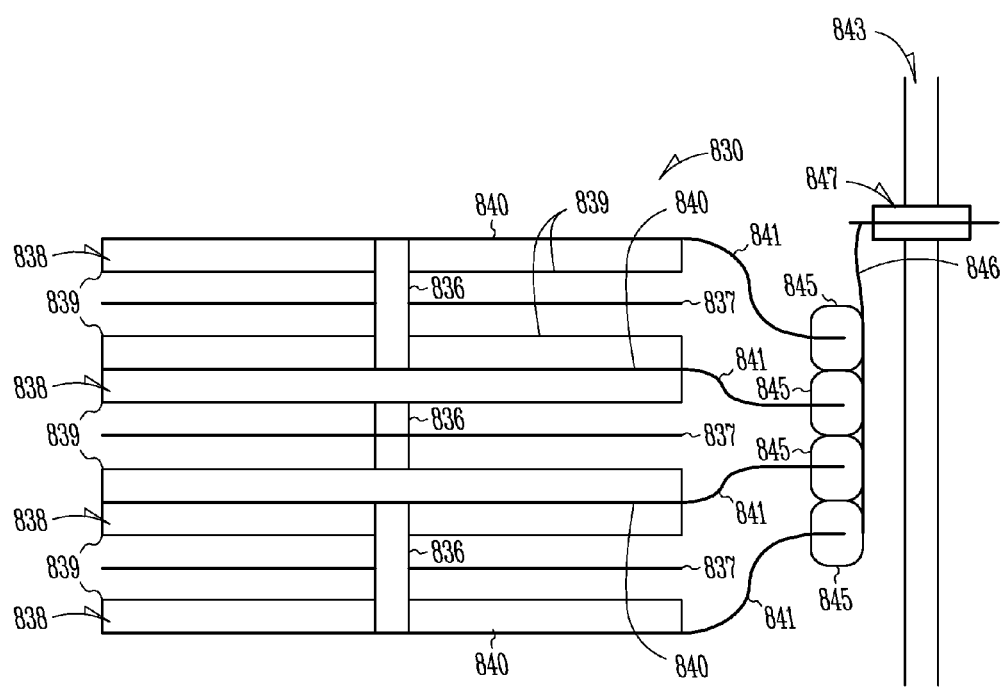

FIGS. 8A and 8B show side views of a capacitor element according to some embodiments of the present subject matter. The capacitor elements 830 include a number of cathode stacks 837, a number of anode plates 838, a number of folded portions 836 coupling anode plates, a number of tabs 841 each coupled to an anode plate, and a clip 845 coupled to each anode tab 841 for electrically coupling the anode plates 838 to each other and, in various embodiments, to other electrical components. Each anode plate 838 includes a sintered material 839 disposed on a substrate 840. The anode plates 838 include sintered material 839 disposed on at least one major surface of an anode plate substrate 840. In various embodiments, sintered material 839 is disposed on both major surfaces of an anode plate substrate 840. In various embodiments, the folded portions 836 connecting the anode plates are continuous portions of the anode plate substrate 840. It is understood that although the illustrated embodiment shows subsequent folding portions extending from opposite sides of the anode plate structure, other orientation arrangements and are possible, as are other anode substrate shapes, without departing from the scope of the present subject matter. The anode tabs 841 may be a continuous piece of the substrate material extending from the perimeter of the anode plate substrate 840. In various embodiments, the tabs 841 may be separate pieces of material coupled to the anode plate, for example, a tab may be coupled to a substantially sintering free portion of the anode plate substrate. The clips 845 coupled to the tabs are welded together to electrically couple the anode plates. In the illustrated embodiment, the clips are coupled to a case 843 enclosing the capacitor element. The clips 845 are coupled to the case 843 using a conductive ribbon 846. In some embodiments, the clips 845 are coupled to a feedthrough 847 of the case 843 using a conductive ribbon 846, as is shown in FIG. 8B.

Figure 9:
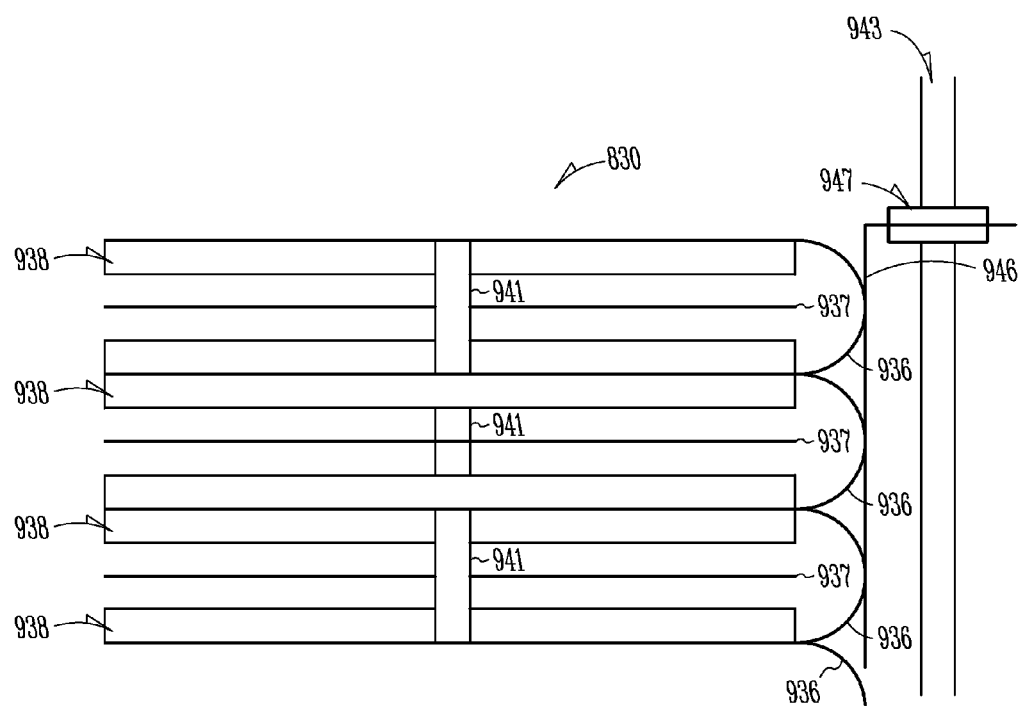
FIG. 9 shows a capacitor element according to some embodiments of the present subject matter.

FIG. 9 shows a capacitor element according to some embodiments of the present subject matter. The capacitor element 930 includes a number of cathode stacks 937, a number of anode plates 938 and folded portions 936 connecting the anode plates. The folded portion 941 of an anode plate interconnects each subsequent anode plate. A ribbon of conductive material 946 is used to interconnect the anode plates using the folded portions. The ribbon of conductive material 946 is coupled to a feedthrough 947 of a case 943 for connection to other electronics, such as electronics related to an implantable medical device. In various embodiments, the conductive material 946, such as a ribbon, may be used to couple the anode plates to the case. In some embodiments, the ribbon interconnects anodes of a single capacitor element. In some embodiments, the ribbon interconnects multiple capacitive elements, for example, using the folded portions of anode plates of each element. In various embodiments, a ribbon is used to interconnect the anode plates 938 and a tab is used to connect the interconnected anode plates to the case or to a feedthrough of the case. In various embodiments, folded portions of the anode plates may be arranged such that additional conductive ribbons may be used to interconnect the anode plates. In some embodiments, the folded portions of the capacitor element, or multiple capacitor elements, are grouped at an offset to allow for partitioning of the capacitor.

Figure 10A:
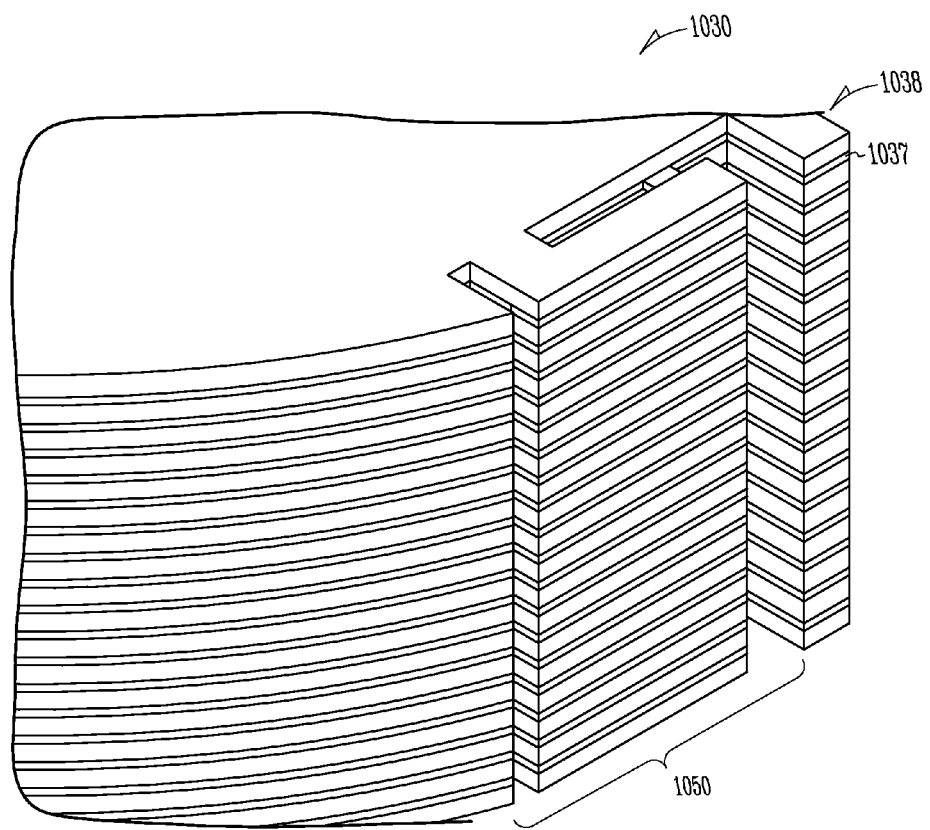
FIGS. 10A and 10B show a capacitor element according to some embodiments of the present subject matter.
Figure 10B:
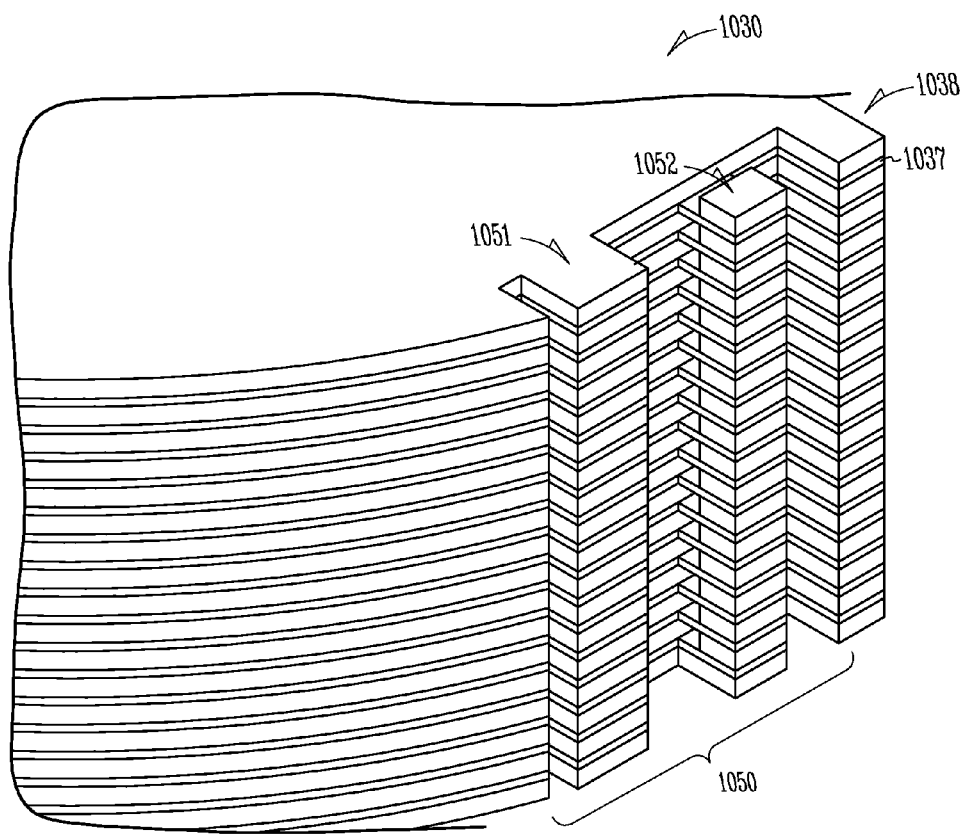

FIGS. 10A and 10B show a capacitor element according to some embodiments of the present subject matter. FIG. 10A shows a partially assembled stack of capacitor components including sintered anode plates 1038 and cathode stacks 1037. Each anode plate and each cathode stack include a notch 1050 with an L-shaped tab extending from an interior side of the notch. When stacked, the legs of the L-shaped tabs of the anode plates overlap the legs of the L-shaped tabs of the cathode stacks. However, the L-shaped protrusions of the anode plates extend from the anode plate at the opposite end of the leg than do the L-shaped tabs extending from the cathode stacks. Once stacked, the legs of the L-shaped protrusions of the anode plates and the cathode stacks are coupled, such as by welding, to form a solid coupling of the tab legs. The middle section of the legs are then excised, such as by laser cutting, mechanical etching, chemical etching or grinding, for example. FIG. 10B shows the structure after the legs of the tabs have been excised. Excising the middle of the legs results in a pair of connected tabs 1051, 1052 forming somewhat rigid connections. A first set of connected tabs 1051 couples the anode plates together, and a second set of connected tabs 1052 couples the cathode stacks together. The above method of forming anode and cathode connection tabs uses materials of the initial anode and cathode structures to form the isolated tabs. The resulting tabs form a rigid stack when welded together. Such tabs provide robust connection points for additional electronics and reduce the risk of damaging the cathode substrate, for example, when handling the capacitor element during processing. Such substrates are often very thin and easily damaged during processing.

Figure 11:
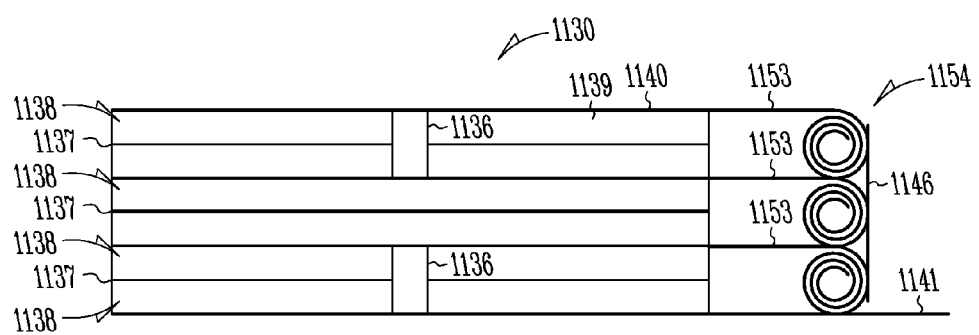
FIG. 11 shows a side view of a capacitor element according to some embodiments of the present subject matter.

FIG. 11 shows side view of a capacitor element according to some embodiments of the present subject matter. The capacitor element 1130 includes a number of cathode stacks 1137, a number of sintered anode plates 1138, and a number of folded portions 1136 coupling anode plates stacked with the cathode stacks. Several of the anode plates include a tab 1153 extending from the anode plate. The tabs are rolled from a distal end back toward the anode plate from which each extends. The diameter of the rolled portion 1154 is approximately equal to the spacing of adjacent anode plates. The rolled portion 1154 of the tabs reduce stress on the tabs that may otherwise exist when connecting the tabs without the rolled portion. In various embodiments, the rolled portion 1154 of the tabs are coupled together, for example with a weld, to form an anode connection. In various embodiments, the tabs are formed from substrate material 1140 of the anode plate on which sintered material 1139 is disposed. In various embodiments, the rolled portion 1154 of the tabs in used to interconnect the anode plates and an unrolled tab 1141 is used for connecting the anodes of the capacitor element to other components of a device, such as an implantable medical device. In some embodiments, a conductive ribbon 1146 is used to couple the rolled tabs together.

This application is intended to cover adaptations or variations of the present subject matter. It is to be understood that the above description is intended to be illustrative and not restrictive. The scope of the present subject matter should be determined with reference to the appended claims, along with the full scope of legal equivalents to which such claims are entitled.

What is claimed is:

1. An apparatus comprising:
    a first electrode;
    a second electrode stacked with the first electrode;
    an interconnect adapted to fold upon itself to couple the first electrode to the second electrode, wherein the first electrode, the second electrode and the interconnect include a unitary substrate;
    a sintered material disposed on the unitary substrate;
    a third electrode stacked between the first and second electrodes; and
    a case enclosing the first electrode, the second electrode, the third electrode and the interconnect.

2. The apparatus of claim 1, wherein the first electrode includes a first tab, and
    wherein the second electrode includes a second tab coupled to the first tab, 3. The apparatus of claim 2, comprising a first clip adapted to couple the first tab with the second tab.

4. The apparatus of claim 2, comprising a first clip coupled to the first tab and a second clip coupled to the second tab, wherein the first clip is coupled to the second clip.

5. The apparatus of claim 1, wherein the first electrode includes a first tab extending from a first location along a perimeter of the first electrode, the first tab including a first connection portion, and wherein the second electrode includes a second tab extending from a second location along the perimeter of the second electrode, the second tab coupled to the second electrode.

6. The apparatus of claim 5, wherein the second tab includes a second connection portion, the first connection portion is coupled to the second connection portion, the first connection portion and the second connection portion are substantially free of sintered material.

7. The apparatus of claim 5, including a clip physically and electrically coupling the first tab and the second tab.

8. The apparatus of claim 5, including:
    a first clip coupled to the first tab;
    a second clip coupled to the second tab; and
    a weld coupling the first clip and the second clip.

9. The apparatus of claim 1, including a case connection coupling the first and second electrode to the case.

10. The apparatus of claim 1, comprising a feedthrough and a ribbon coupling the first and second electrodes to the feedthrough.

11. The apparatus of claim 1, including additional electrodes, the additional electrodes stacked with the first and second electrodes, wherein the additional electrodes each include a respective interconnect of a plurality of interconnects, the plurality of interconnects folded together and electrically coupled with one another.

12. The apparatus of claim including a ribbon physically and electrically coupling the plurality of interconnects.

13. The apparatus of claim 12 wherein the ribbon is coupled to the case.

14. The apparatus of claim 12, including a feedthrough coupled to the case, wherein the ribbon is coupled to the feedthrough, and the feedthrough electrically insulates the ribbon from the case.

15. The apparatus of claim 1, wherein the unitary substrate is a foil that is solid and monolithic.

16. A method, comprising:

sintering a first material onto a first substrate portion of a unitary substrate to form a first electrode;

sintering a second material onto a second substrate portion of the unitary substrate to form a second electrode;

folding an interconnect of the unitary substrate upon itself, wherein the first electrode is coupled to the second electrode by the interconnect, and stacking the first electrode onto the second electrode;

stacking a third electrode between the first and second electrodes; and enclosing the first electrode, the second electrode, the third electrode and the interconnect in a case.

17. The method of claim 16, comprising forming a first tab out of material from a portion of the first substrate, and forming a second tab out of material from the second substrate.

18. The method of claim 17, comprising clipping the first tab and the second tab with a clip.

19. The method of claim 17, comprising clipping a first clip to the first tab; clipping a second clip to the second tab; and coupling the first clip and the second clip.

20. The method of claim 19, comprising welding the first clip to the second clip.

* * * * *